United States Patent [19]
Saadat et al.

[11] Patent Number: 5,935,137
[45] Date of Patent: Aug. 10, 1999

[54] TUBULAR FALLOPIAN STERILIZATION DEVICE

[75] Inventors: Vahid Saadat, Redwood Shores; James R. Kermode, Sunnyvale, both of Calif.

[73] Assignee: Gynecare, Inc., Menlo Park, Calif.

[21] Appl. No.: 08/897,069

[22] Filed: Jul. 18, 1997

[51] Int. Cl.[6] .................................................. A61D 1/06
[52] U.S. Cl. ......................... 606/135; 606/136; 606/137; 606/29; 606/30; 606/33; 128/830; 128/831; 128/839
[58] Field of Search ............................... 606/135; 600/33, 600/30, 29; 128/830–842, 1 R, 215, 235, 831–845

[56] References Cited

U.S. PATENT DOCUMENTS

| 3,042,030 | 7/1962 | Read ........................................ 128/127 |
| 3,404,682 | 10/1968 | Waldron .................................. 128/285 |
| 3,405,711 | 10/1968 | Bakunin .................................. 128/130 |
| 3,422,813 | 1/1969 | Braley et al. ............................... 128/1 |
| 3,463,141 | 8/1969 | Mozolf ....................................... 128/1 |
| 3,467,090 | 9/1969 | Zollett ..................................... 128/131 |
| 3,598,115 | 8/1971 | Horne, Jr. ............................... 128/130 |
| 3,675,642 | 7/1972 | Lord .......................................... 128/1 |

(List continued on next page.)

FOREIGN PATENT DOCUMENTS

| 0105669 | 4/1984 | European Pat. Off. ...................... 5/46 |
| 0241971 | 10/1997 | European Pat. Off. ............... 128/839 |
| 2010728 | 7/1979 | United Kingdom ................... 128/831 |
| WO 094024944 | 11/1994 | WIPO .................................... 128/831 |

OTHER PUBLICATIONS

Corfman, An instrument for transcervical treatment of the oviducts and uterine cornua, vol. 27, No. 6, Jun. 1996, p. 883.

Brueschke, E., Zaneveld, L., Wilbanks, G., Archie, J., Uretz, E., "Steerable Hysterscope and Mechanical Tubal Occlusive Devices," Hysteroscopy, Advances in Female Sterilization Techniques, 1982, pp. 182–198.
Brudin, J., "Hydrogel Tubal Blocking Device: P–Block," Female Transcervical Sterilization, 1982, pp. 240–244.
Cooper, J., "Hysteroscopic Sterilization," Fertility Control, Second Edition, 1984, pp. 363–376.
Cooper, J., and Houck, R., "Study Protocol, Criteria, and Complications of the Silicone Plug Procedure," Female Transcervical Sterilization, 1982, pp. 256–269.
Cooper, J., Houck, R., Rigberg, H., "The Incidence of Intrauterine Abnormalities Found at Hysteroscopy in Patients Undergoing Elective Hysteroscopic Sterilization," The Journal of Reproductive Medicine, vol. 28, No. 10, Oct. 1993, pp. 659–661.

(List continued on next page.)

*Primary Examiner*—Gary Jackson
*Assistant Examiner*—Lien Ngo
*Attorney, Agent, or Firm*—Verne E. Kreger, Jr.

[57] ABSTRACT

An apparatus and method for human female sterilization. The apparatus includes an occlusive device configured from an elongate tubular member having a central lumen and a flange formed at the proximal end. The occlusive device is formed with a plurality of flexible ribs configured to provide a plurality of seals within the interstitial portion of a Fallopian tube. A valve member is preferably disposed within the lumen of the tubular member. The occlusive device may further include a plurality of copper rings disposed between the ribs of the tubular member, or ribs may be coated with a material containing copper. The method includes placing the occlusive device within a delivery catheter having a lumen and placing the distal end of the delivery catheter within the uterus. After the occlusive device and distal end of the delivery catheter are placed in the Fallopian tube, the occlusive device is removed from the delivery catheter and ejected into the Fallopian tube. In addition, a guide wire may be inserted through the vagina and into a Fallopian tube of the uterus such that the occlusive device and the delivery catheter are threaded over the guide wire.

21 Claims, 12 Drawing Sheets

U.S. PATENT DOCUMENTS

| | | | |
|---|---|---|---|
| 3,680,542 | 8/1972 | Climber | 128/1 |
| 3,687,129 | 8/1972 | Nuwayser | 128/1 |
| 3,768,102 | 10/1973 | Kwan-Gett et al. | 3/1 |
| 3,803,308 | 4/1974 | Zipper | 128/833 |
| 3,858,571 | 1/1975 | Rudolph | 128/1 R |
| 3,918,431 | 11/1975 | Sninnreich | 128/1 |
| 3,973,560 | 8/1976 | Emmett | 128/833 |
| 4,135,495 | 1/1979 | Borgen | 128/1 |
| 4,136,695 | 1/1979 | Dafoe | 128/215 |
| 4,158,050 | 6/1979 | Zipper | 424/314 |
| 4,160,446 | 7/1979 | Barrington | 128/1 |
| 4,181,725 | 1/1980 | Voorhees et al. | 424/258 |
| 4,185,618 | 1/1980 | Correy | 128/1 |
| 4,245,623 | 1/1981 | Erb | 128/1 |
| 4,365,621 | 12/1982 | Brundin | 128/1 |
| 4,374,523 | 2/1983 | Yoon | 128/326 |
| 4,416,660 | 11/1983 | Dafoe | 604/55 |
| 4,485,814 | 12/1984 | Yoon | 128/327 |
| 4,509,504 | 4/1985 | Brundin | 128/1 |
| 4,579,110 | 4/1986 | Hamou | 128/130 |
| 4,595,000 | 6/1986 | Hamou | 128/130 |
| 4,601,698 | 7/1986 | Moulding, Jr. | 604/55 |
| 4,606,336 | 8/1986 | Zeluff | 128/130 |
| 4,700,701 | 10/1987 | Montaldi | 128/303 |
| 4,731,052 | 3/1988 | Seitz, Jr. | 604/51 |
| 4,788,966 | 12/1988 | Yoon | 128/831 |
| 4,808,399 | 2/1989 | Rypácek et al. | 424/2 |
| 4,824,434 | 4/1989 | Seitz, Jr. | 604/27 |
| 4,932,422 | 6/1990 | Ragheb | 128/839 |
| 4,937,254 | 6/1990 | Sheffield et al. | 514/420 |
| 4,983,177 | 1/1991 | Wolf | 606/157 |
| 5,065,751 | 11/1991 | Wolf | 128/831 |
| 5,095,917 | 3/1992 | Vancaillie | 128/831 |
| 5,478,837 | 12/1995 | Rodgers et al. | 514/297 |
| 5,634,877 | 6/1997 | Salama | 600/29 |
| 5,725,777 | 3/1998 | Taylor | 210/650 |
| 5,795,288 | 8/1998 | Cohen et al. | 600/29 |

OTHER PUBLICATIONS

Corfman, P.A., Taylor, Jr., H., National Institutes of Health, Bethseda, Md., "An Instrument For Transcervical Treatment of the Oviducts and Uterine Cornua," Obs. & Gynec., vol. 27, No. 6, 1996, pp. 880–884.

Craft, I., "Uterotubal Ceramic Plugs," Advances in Female Sterilization Techniques, 1982, pp. 176–181.

Darabi, K., Roy, K., and Richart, R., "Collaborative Study on Hysteroscopic Sterilization Procedures: Final Report," Workshop on Risks, Benefits, and Controversies in Fertility Control, Arlington, VA, 1977, pp. 81–101.

Eddy, C., and Pauerstein, C., "Anatomic and Physiologic Factors Affecting the Development of Transcervical Sterilization Techniques," Female Transcervical Sterilization, 1982, pp. 7–23.

Edström, K. and Fernström, I., The Diagnostic Possibilities of a Modified Hysteroscopic Technique, Acta Obstet Gynec Scand 49:327–330, 1970.

Erb, R., "Hysteroscopic Tubal Occlusion Procedure With Formed–in–Place Silicone Plugs: Instruments and Technique," Female Transcervical Sterilization, 1982, pp. 245–254.

Erb, R., and Reed, T., "Hysteroscopic Oviductal Blocking with Formed–in–Place Silicon Rubber Plugs," The Journal of Reproductive Medicine, vol. 23, No. 2, Aug. 1979, pp. 65–68.

Hamou, J., "Hysteroscopy and Microhysteroscopy With a New Instrument: The Microhysteroscope," Acta Europea Fertilitatis, vol. 12, No. 1, Mar. 1981, pp. 29–58.

Hefnawi, F., Fuchs, A., Laurence, K., "Control of fertility by temporary occulusion of the oviduct," Am.J.Obst. & Gynec., vol. 99, No. 3, Oct. 1, 1967, pp. 421–427.

Hosseinian, A., Lucero, S., Kim, M., "Hysteroscopic Implantation of Uterotubal Junction Blocking Devices," Advances in Female Sterilization Techniques, 1982, pp. 169–175.

Hosseinian, A., Morales, W., "Clinical Application of Hysterscopic Sterilization Using Uterotubal Junction Blocking Devices," Female Transcervical Sterilization, 1982, pp. 234–239.

Houck, R., and Cooper, J., "Hysteroscopic Tubal Occlusion With Formed–in–Place Silicone Plugs," Obstetrics & Gynecology, vol. 60, No. 5, Nov. 1982, pp. 641–644.

Houck, R., Cooper, J., and Rigberg, H., "Hysteroscopic Tubal Occlusion With Formed–In–Place Silicone Plugs: A Clinical Review," Obstetrics & Gynecology, vol. 62, No. 5, Nov. 1983, pp. 587–591.

Lindermann, H., and Mohr., Jr., "$CO_2$ Hysteroscopy: Diagonosis and Treatment,"Am. J. Obstet. Gynecol., vol. 124, No. 2, Jan. 15, 1976, pp. 129–133.

Menken, F., Ein neues Verfahren mit Vorrichtung zur Hysterskopie,: 14 Endoscopy Apr. 1971, pp. 200–203.

Quiñone, R., Alvarado, A., and Ley, E., "Hysteroscopic Sterilization," Int J Gynaecol Obstet 14:27–34, 1976.

Reed, T., and Erb, R., "Hysteroscopic Female Sterilization with Formed–in–Place Silicone Rubber Plugs," Endoscopic Female Sterilization—A Comparison of Methods, 1983, pp. 143–154.

Reed, T., and Erb, R., "Hysteroscopic Oviductal Blocking with Formed–in–Place Silicone Rubber Plugs—II. Clinical Studies, " The Jur. of Reproductive Medicine, vol. 23, No. 2, Aug. 1979, pp. 69–72.

Reed, T., and Erb, R., "Tubal Occlusion with Silicone Rubber—An Update, " The Journal of Reproductive Medicine, vol. 25, No. 1, Jul. 1980, pp. 25–28.

Reed, T., Erb, R., DeMaeyer, J., "Tubal Occlusion with Silicone Rubber," The Journal of Reproductive Medicine, vol. 26, No. 10, Oct. 1981. pp. 534–537.

Richart, R., Neuwirth, R., Nuwayser, E., Fenoglio, C., "Evaluation of Polymer Flock and Metal Alloy Intra–Tubal Device in Pigtail Monkeys," Contraception, vol. 128, No. 5, Nov. 1978, pp. 459–468.

Rimkus, V., and Semm, K., "Hysteroscopic Sterilization—a Routine Method?" Int. J. Fetil 22, 1976, pp. 121–124.

Sciarra, J., "Heteroscopic Approaches for Tubal Closure," Research Frontiers in Fertility Regulation, 1980, pp. 270–286.

Siegler, A., and Grunebaum, A., "The 100th Anniversary of Tubal Sterilization," Fertility and Sterility, vol. 34, No. 6, Dec. 1980, pp. 610–613.

Silander, T., "Hysteroscopy Through a Transparent Rubber Balloon,"Surgery, Gynecology & Obstetrics, Jan. 1962, pp. 125–127.

Silander, T., "Hysteroscopy Through a Transparent Rubber Balloon in Patients with Carcinoma of the Uterine Endometrium," Acta obst. Et. gynec. Scandivan. 42, 1963, pp. 284–300.

Sugimoto, O., "Hysteroscopic Sterilization by Electrocoagulation," Hysteroscopic Sterilization, 1973, pp. 107–120.

Sweeney, W., "The Interstitial Portion of the Uterine Tube— Its Gross Anatomy, Course, and Length," Obstetrics and Gynecology, vol. 19, No. 1, Jan. 1962, pp. 3–8.

TUBULAR FALLOPIAN STERILIZATION DEVICE

BACKGROUND OF THE INVENTION

The present invention relates generally to an apparatus and method for female sterilization and more particularly to a system for occlusion of the Fallopian tubes of a human uterus having a tubular blockage device insertable with a catheter in which the blockage device is disposed prior to deployment. The following terms as used herein have the meaning given below:

"Endometrium" is that portion of the inner lining of the uterus to which an embryo normally attaches and is responsible for the menstrual cycles.

"Proximal" is that portion closest to the physician or furthest outside the patient.

"Distal" is that portion furthest from the physician or furthest inside the patient.

"Interstitial segment" is the portion of the Fallopian tube which is immediately distal to the opening of the tube into the uterine cavity.

"Isthmic segment" is the portion of the Fallopian tube which is distal to the interstitial segment.

"Fimbrial segment" is the portion of the Fallopian tube which is distal to the isthmic segment.

It has been widely recognized that the explosive growth in the world population, creates a serious problem for the future of our society. Thus, there is a need to develop a safe and effective contraceptive device and/or method. Although the surgical sterilization of women may be the most effective and widely used method of contraception known, current procedures, such as radical hysterectomy, is not always warranted or desirable. Consequently, a need exists for the development of a nonsurgical method for effecting sterilization which can be performed by a gynecologist within a non-hospital setting and which does not require extensive facilities or equipment.

The ideal sterilization procedure should be safe, as well as effective. The method and/or device should be applicable to ambulatory patients with the use of local anesthesia or without anesthesia, since many of the complications that relate to sterilization procedures are complications that occur with the use of anesthetic agents. It should be socially and personally acceptable; it should be inexpensive and applicable to large numbers of patients; and it should be potentially reversible in the event of a change in desire for fertility potential on the part of the patient.

Although many techniques of female sterilization have been described, tubal sterilization shows increasing acceptance for providing safe and effective contraception. A wide range of transcervical techniques for female sterilization have been documented. Previous efforts to achieve this goal have included the infusion of various scarifying and necrotizing agents, tissue glues and tubal plugs into the uterus for the purpose of effecting an occlusion of the oviducts or Fallopian tubes. The use of a hysteroscope for direct visual approach to the tubal ostia has been suggested to enhance such a procedure. The female reproductive anatomy presents natural barriers to sterilization.

The oviducts are paired, hollow, seromuscular organs that extend from the superior-lateral aspect of the uterine fundus to the ovaries. Each oviduct is supported throughout its length by a peritoneal fold, the mesosalpinx, and is bordered anteriorly by the round ligament and posteriorly by the ovarian ligament and mesovarium. The oviduct is attached medially to the uterine fundus and laterally to the infundibular pelvic ligament and ovary by way of an elongated mucosal fold, the fimbria ovarica.

The extrauterine oviduct is sheathed throughout its length by a serosal covering consisting of a layer of loose connective tissue covered by a single layer of mesothelium continuous with the mesosalpinx. Beneath the mesothelial layer, smooth muscle fibers, distinct from those of the tubal muscularis are present. The connective tissue is highly vascular and contains numerous lymphatic vessels. These originate primarily along the mesosalpingeal border, extend parallel to the oviduct, and branch extensively, penetrating into the muscular and mucosal layers of the oviduct.

Because of the arrangement of muscle fibers in layers oriented in circular and longitudinal fashion, the oviduct is capable of generating a variety of contractile patterns, including peristaltic, antiperistaltic, and segmental contractions. Unlike the alimentary tract, the oviduct does not generate regular peristaltic contractions. Instead, it demonstrates segmental contractions that propagate simultaneously in opposite directions over short distances. Ovum transport, therefore, assumes a discontinuous pattern of reciprocal movements in which the ovum is forced out of areas of contraction into inactive regions. Thus, ovum transport appears to occur in a series of random movements that, over several days, acquire a gradual net bias toward the uterus.

Whether "blind" or hysteroscopically directed, transcervical sterilization procedures can be divided into three categories based upon the mechanism of tubal occlusion. Sterilization can be effected by (1) destruction of the interstitial portion of the oviduct by thermal energy (electrocoagulation or cryosurgery); (2) injection techniques for the delivery of sclerosing substances or tissue adhesives; and (3) mechanical occlusive devices or plugs to block the oviduct.

In the early 1970's, a number of investigators developed experience with electrocoagulation as a technique for hysteroscopic sterilization. Tubal occlusions were performed by applying a coagulating current to the interstitial portion of the Fallopian tube with a metal ball-tip electrode to coagulate the tubal epithelium. Alternatively, a silastic tipped electrode was introduced into the interstitial or isthmic portion of the tube to a depth to avoid unnecessary complications. Tubal electrocoagulation under hysteroscopic control was performed on uteri using different coagulation times and intensities of current. A coagulation current was applied to the tubal epithelium until the tissue became white and small air bubbles were seen while the coagulation current was applied. The electrode was then removed from the tube and the procedure repeated on the contralateral Fallopian tube. Another approach to transcervical sterilization utilized cryosurgical techniques to produce necrosis of the endometrium and subsequent scar formation of the cornual areas of the uterus. Such cryosurgery caused coagulation necrosis of the tissue, due to severe biochemical and biophysical changes produced by the sub-freezing temperatures.

Several injection techniques for the delivery of sclerosing substances or tissue adhesives have been attempted. One such technique includes passing a nitric acid-coated probe through a woman's cervix to chemically stricture the tubal ostia. Another procedure comprised hysteroscopically controlled quinacrine infusion in the tubal ostia. Another procedure utilized an assembly for positioning and guidance of a hypodermic needle for blind injection of an inflammatory or sclerosing agent at the cornual portion of the tubal lumen on opposite sides of the uterus. However, the failure rate with such techniques was so high that such techniques have been generally abandoned.

Alternate chemical blocking procedures include infusing catalyzed viscous silicone rubber into the uteri of animals. Similarly, occlusion of the oviducts with silicone rubber was tried for sterilization. The procedure comprised a system and application technique for a nonincisional method for blocking the Fallopian tubes with medical-grade silicone rubber. Under hysteroscopic control, catalyzed liquid silicone polymer flows into the oviduct through a silicone rubber obturator tip positioned at the tubal ostium. The formed-in-place plug becomes bonded to the obturator tip. The resulting flexible structure is larger in diameter at both ends than it is in the isthmus and thus remains in place to achieve tubal occlusion. One major disadvantage is the need for sophisticated equipment and technology. Another limitation is the time demand on the physician and assistant. An additional concern is the potential for inadvertent disruption of the plugs at the time of a diagnostic dilatation and curettage, should this be indicated at some later date.

Recent attention has focused on the concept of mechanically blocking or occluding the oviducts with intratubal devices. Such devices include an inert cornual plug designed to obstruct entry to the Fallopian tubes having an overall bullet configuration having a cone-shaped forward portion that cooperates with the uterine walls. The device included a wire anchoring means extending from about the mid-portion of the plug to secure the plug in position by anchoring it to the cornual area of the uterus. The cornual plug is optionally provided with a pendant string or cord for removal of the device.

Also known is a spherical device that is inserted in the Fallopian tube to plug the passageway and prevent the passage of an egg or ovum from the Fallopian tubes into the uterus. Also described is an intrauterine contraceptive device that is generally V-shaped having a pair of slender divergent arms formed with bulbous extremities that are said to tend to become located in the Fallopian region of the uterus when the stem portion of the device is in the os. Others have developed a hydrogelic tubal blocking device fixed on a firm nylon skeleton. In addition, the tubal occlusion properties of ceramic plugs has been studied.

Other known tubular occlusive devices included a polyethylene plug that measured approximately ten millimeters in length with a diameter of one millimeter at the tip and two millimeters at the base. Further, plugs formed from inert, radiopaque, surgical nylon were placed in the tubal ostia with the use of the colpomicrohysteroscope. The nylon device has an open loop with elastic "memory" at each extremity to prevent migration within the Fallopian tube. The midpiece, measuring twenty-three millimeters in length and one millimeter in diameter, is flexible and permits negotiation of the interstitial portion of the tube. Removal of the plug is easily effected by traction on the proximal loop.

Still another intratubal device was made of preformed silicone rubber and is packed in advance into an introducer made of Teflon tubing 1.5 millimeters in diameter. The plug was generally tubular having a segmented body and a proximal portion configured to engage the tubular ostia and for removal of the device. An obturator wire pushes the plug out of the introducer into the tubal ostia under direct hysteroscopic visualization. Such a device was reported in *Fertility Control,* Corson et al. Eds., 2d edition 1994, Goldin Publishers, London, Ont., p. 369 (see FIG. 6 re Sugimoto device). Placement of some such occlusive plugs were reportedly accomplished during an outpatient visit, utilizing no anesthesia. Carbon dioxide was utilized for uterine distention in certain techniques.

Although the prior art has attempted various means of female human sterilization, many such methods have proven ineffective over time. Thus, heretofore, there has been a need for a minimally invasive female sterilization system that ensures complete, but reversible, blockage of the Fallopian tubes to provide safe and effective sterilization.

SUMMARY OF THE INVENTION

The present invention relates generally to an apparatus and method for female sterilization and more particularly to a system for occlusion of the Fallopian tubes of a human uterus having a tubular blockage device insertable with a catheter in which the blockage device is disposed prior to deployment. The present invention includes a tubular blockage device having a size and shape configured to be removably implanted into the Fallopian tubes of a human uterus. The blockage device has a distal end configured in a conical tip and a plurality of arcuate ribs forming a body. The proximal end is configured with a peg-like flange for securing to a removal device. A central lumen traverses from the proximal end to the distal end of the blockage device body for insertion of a guide wire or for alternative functions, such as reversibility of sterilization.

One embodiment of the present invention includes a sealing core in the lumen of the blockage device body. Another embodiment of the present invention further includes a hydrogel sealing core in the lumen of the blockage device body. In another embodiment of the present invention, the blockage device body includes a lumen for retaining a guide wire. Such a lumen may also include duck bill valves disposed in the proximal end and the distal end of the lumen of the blockage device. Yet another embodiment of the present invention includes a plurality of bristles disposed within the lumen of the blockage device body.

The method of use of the device of the present invention includes inserting a guide wire into the Fallopian tube. A blockage device is inserted over the guide wire. A sheath or delivery catheter is used to push the blockage device into place. The uterine cavity and Fallopian tube are examined with a hysteroscope, with x-ray imaging or with a similar visualization system so as to estimate the position of the blockage device. Once the blockage distal is in the desired position, the guide wire is withdrawn while keeping the blockage device in position using the sheath. The device is then left in place within the interstitial or isthmic segment of the Fallopian tube.

The occlusive device of the present invention configured for human female sterilization includes an elongate tubular member having a central lumen therethrough. The device is configured with a flange formed at the proximal end of the elongate tubular member and a plurality of ribs formed between the proximal end and the distal end of the tubular member. A valve member is preferably disposed within the lumen of the tubular member. The ribs of the tubular member are preferably constructed of an elastomeric material. The occlusive device may further include a plurality of copper rings disposed between the ribs of the tubular member, or ribs may be coated with a material containing copper.

The method for human female sterilization of the present invention includes inserting an occlusive device of the present invention into a Fallopian tube of human female uterus. The method further includes placing the occlusive device within a delivery catheter having a lumen and placing the distal end of the delivery catheter within the uterus. After the occlusive device and distal end of the delivery catheter are placed in the Fallopian tube, the occlusive device is removed from the delivery catheter and ejected into the Fallopian tube. In addition, a guide wire may be inserted through the vagina and into a Fallopian tube of the uterus. The occlusive device and the delivery catheter are then threaded over the guide wire.

These and other features and advantages of the present invention will become apparent from the following more detailed description, when taken in conjunction with the accompanying drawings which illustrate, by way of example, the principles of the invention.

DETAILED DESCRIPTION OF THE INVENTION

As shown in the drawings for purposes of illustration, the present invention is embodied in an apparatus and method for female sterilization and more particularly to a system for occlusion of the Fallopian tubes of a human uterus having a tubular blockage device insertable with a catheter in which the blockage device is disposed prior to deployment. The present invention includes a tubular blockage device having a size and shape configured to be removably implanted into the Fallopian tubes of a human uterus. The blockage device has a distal end configured in a conical tip and a plurality of arcuate ribs forming a body. The proximal end is configured with a peg-like flange for securing to a removal device. A central lumen traverses from the proximal end to the distal end of the blockage device body for insertion of a guide wire or alternative functions, such as reversibility of sterilization.

Figure 1:
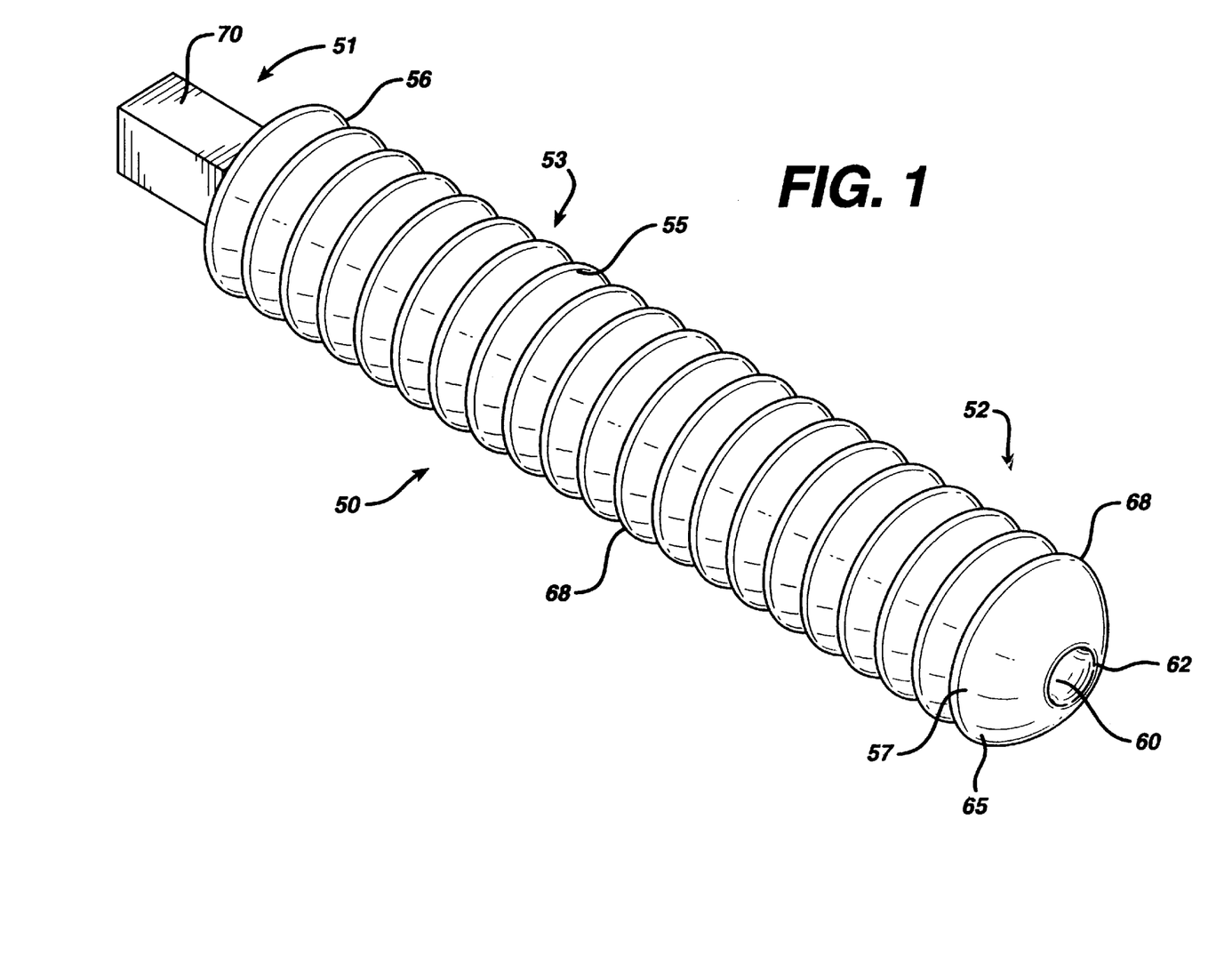
FIG. 1 is perspective view of one embodiment of the Fallopian tube blockage device of the present invention.
Figures 2, 3:
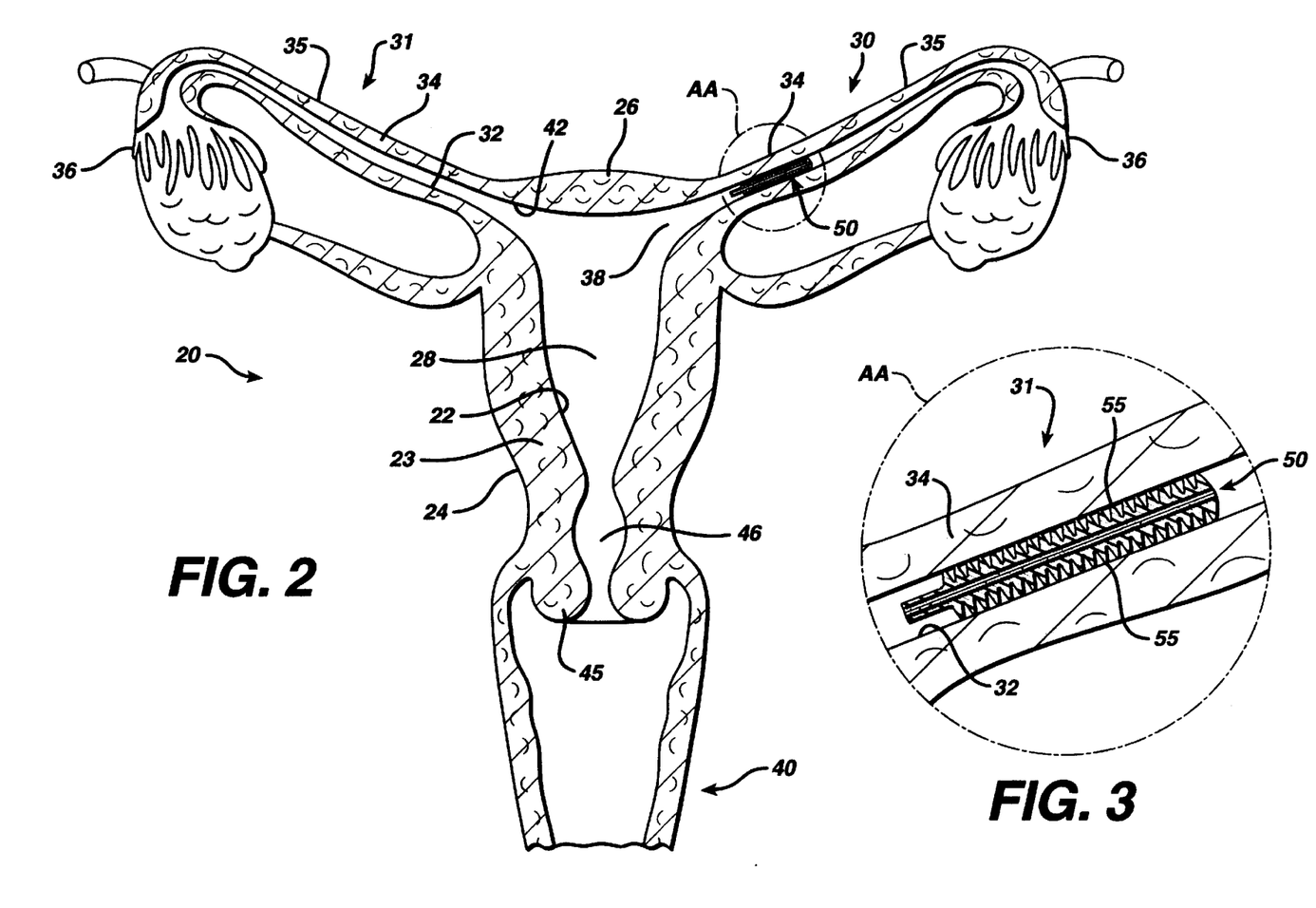
FIG. 2 is a partial cross-sectional of a blockage device of the present invention disposed within a Fallopian tube of a human uterus.
FIG. 3 is an enlarged side sectional view of the portion of the Fallopian tube containing the blockage device of the present invention as shown along circle A—A in FIG. 2.

In accordance with the present invention, and as shown in FIG. 1, a Fallopian tube occlusive device 50 is configured for insertion into a Fallopian tube 30, 31 of a human uterus 20 (see FIG. 2). The tubular occlusive device is specifically configured to provide blockage of the Fallopian tube to prevent spermatozoa or ovum from travelling through the Fallopian tube. The device is preferably of a tubular shape having a generally circular circumference similar to that of the interstitial portion 34 of the Fallopian tube. The present invention is specifically directed to solving the problem of similar prior art devices travelling through the Fallopian tube and being expelled into the uterine cavity 28.

The present invention includes a tubular occlusive device 50 having a plurality of arcuate ribs 55 each resembling an umbrella or a mushroom cap. The plurality of arcuate ribs or blades form a body 53 extending from the distal conical tip 65 to the proximal end 51 which is configured for operably engaging a removal device. These ribs or flukes are generally spaced evenly apart at an interval 59 (see FIG. 6) of one millimeter (mm) for an approximate distance of 1.5 centimeters (cm). The distal end 52 of the occlusive device comprises a conical tip having a distal opening 62 in the center of the most distal rib 57 of the tip. The conical tip orifice is in fluid communication with a lumen 60 throughout the body of the blockage device; however, a valve is preferably placed within the lumen.

The tubular occlusive device So is generally flexible as to conform to the interior contortions of the Fallopian tube 30, 31 in vivo. Each of the arcuate ribs 55 forming the body 53 of the occlusive device is comprised of a circular edge 68 forming a portion of the circumference of the body of the device. The edge is a termination of a convex rib which may be segmented for additional flexibility. The ribs are approximately two-hundred and fifty microns thick while having a circumference of approximately twelve millimeters and a radius of approximately two millimeters.

The body 53 of the tubular occlusive member 50 may be made of a flexible material such as a plastic, a rubber (e.g., latex, silicone) or a suitable biocompatible polymer or elastomer. Similarly, the occlusive device may be made of a liquid crystal polymer, polyurethane, polyethylene, woven-helically wrapped stainless steel or similarly configured material wherein the ribs of the occlusive device are sufficiently flexible. Likewise, the properties of materials such as nitinol may be used to adjust the stiffness, flexibility and shape of the ribs and body of the Fallopian tube occlusive device.

With reference to FIG. 2, the distal end of the blockage device is configured to be inserted within the uterus 20 of a human patient without traumatizing or damaging patient tissue. The uterus is comprised of three basic layers, i.e., the endometrium 22, the myometrium 23 and the outer layer or serosa 24. The blockage device is inserted into the uterus through the cervix 45 and proximate the cornu 38.

Referring again to FIG. 2, the tubular occlusive device 50 is implanted into the interstitial segment 34 of the Fallopian tubes 30, 31. The proximal end 51 of the occlusive device, when properly implanted, is disposed near the cornu 38 of the uterus 20 so that a retraction device may easily grasp or otherwise be secured to the occlusive device when the uterus is distended. The distal end 52 of the blockage device is positioned just proximal the Fallopian tube isthmic segment 35 and significantly proximal the fimbrial segment 36. A properly sized occlusive device firmly engages the Fallopian tube wall 32 as shown in FIG. 3. The diameter of the arcuate ribs 55 should be slightly larger than the diameter of the widest portion of the Fallopian tube in which the occlusive device is to be implanted. The outer diameter of the occlusive device ribs should be about 1.1 to 10.0 times the inner diameter of the Fallopian tube interstitial segment. Should the occlusive device be significantly narrower than the Fallopian tube, then the device may be easily expelled by the natural ovum transport functions, such as segmental contractions. The occlusive device is provided with a lumen 60 from the proximal and to the distal end in which a guide wire may be disposed.

Figure 4:
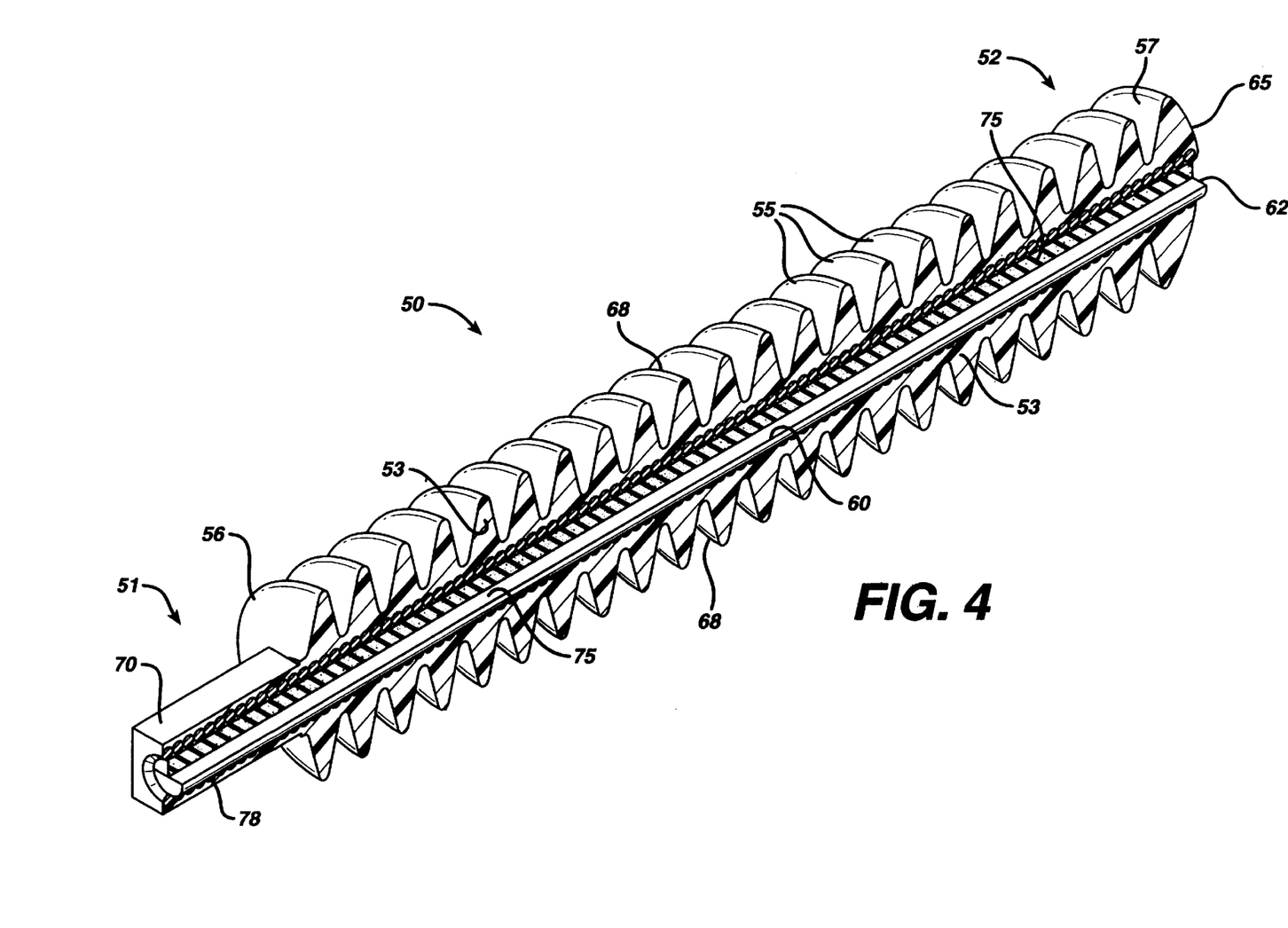
FIG. 4 is a sectional perspective view of the blockage device of an embodiment of the present invention having a sealing core in the lumen of the blockage device body.

As illustrated in FIG. 4, the central lumen 60 of the occlusive device 50 may be filled with a semi-rigid sealing material 75, such as foam rubber, or a viscoelastic polymer. The occlusive device lumen is filled with the sealing material so as to provide a seal around the guide wire and a barrier within the lumen when the guide wire is removed. The present invention anticipates a guide wire required for placement of the occlusive device in the range of 0.014 to 0.032 inches (0.4 to 0.8 mm). Without the sealing member within the lumen, it is possible that spermatozoa may travel through an open lumen potentially causing a tubal pregnancy distal of the distal end of the device. Similarly, it is possible that an ovum could travel through an open lumen of the occlusive device, potentially allowing for fertilization an conception.

As is also shown in FIG. 4, the lumen 60 of the occlusive device is preferably lined with a spring-like support member 78. The support member lines the lumen of the blockage device and from the proximal end 51 to the distal end 52 of the device. The sealing member may be made of a slit solid tube of elastomer, for example, silicone rubber or neoprene rubber. The split seal provides a barrier around the guide wire 95 when the guide wire is disposed within the lumen 60 of the occlusive device 50. When the guide wire is removed the two halves of the split foam filling collapse to form essentially a fluid-tight seal. The foam filler may be impregnated with one or more desired chemicals, including a spermicide.

Figure 5:
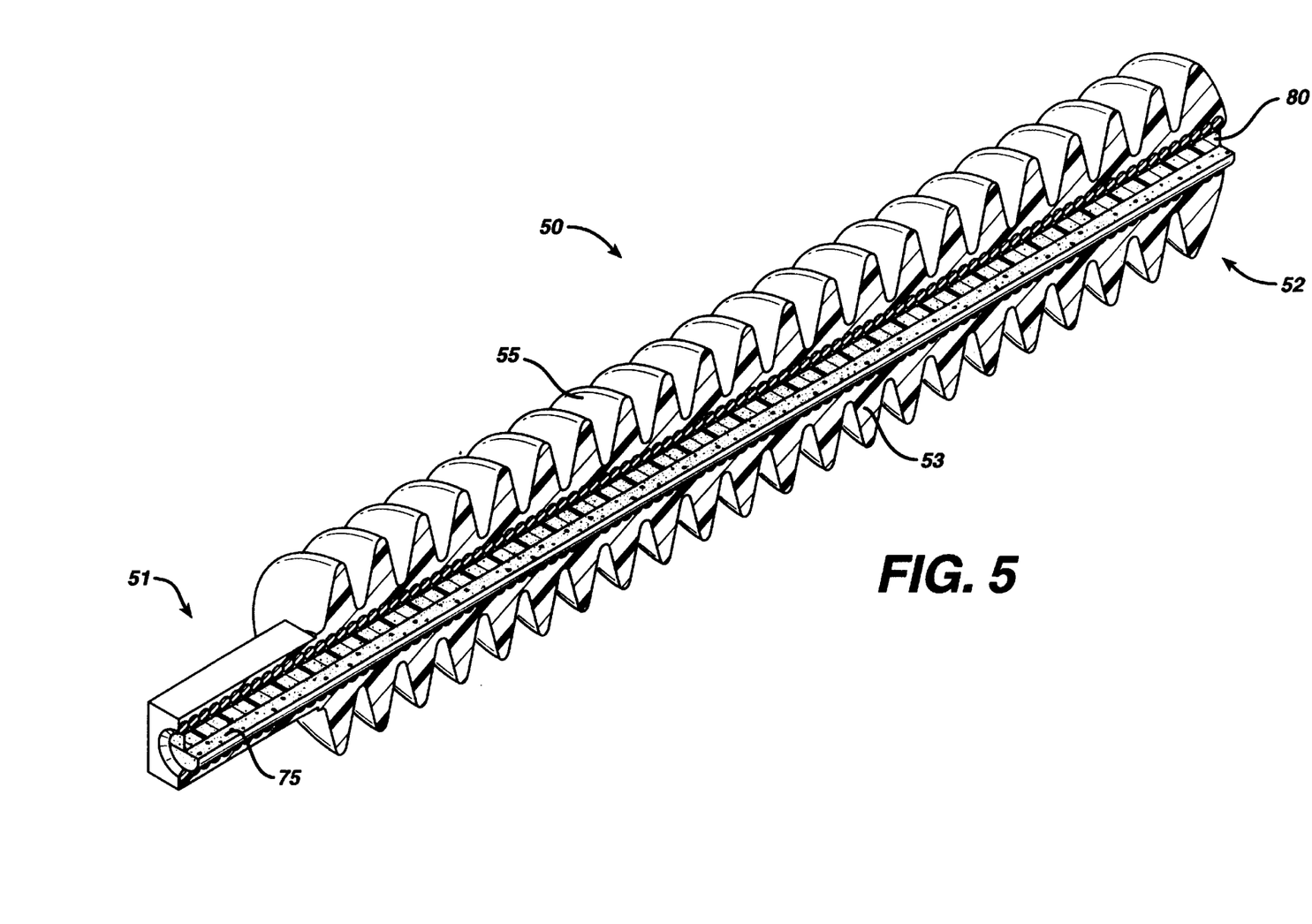
FIG. 5 is a sectional perspective view of the blockage device of an embodiment of the present invention having a hydrogel sealing core in the lumen of the blockage device body.

As shown in FIG. 5, the valve material 80 within the occlusive device lumen 60 may be made from a hydrogel which may be impregnated with a spermicide. Suitable hydrogels are polymers and copolymers of the acrylic type, for example cross-linked polyacrylamide and polymers and copolymers of methacrylic acid esters with at least one hydroxy group in the side chain. Suitable monomers are 2-hydroxy-ethyl-methacrylate, in which case the ester groups can originate from diethylene glycol or triethylene glycol. For example, 2,3-dihydroxy-propyl-methacrylate may also be used. Polyfunctional acrylates such as diesters or corresponding glycols, for example ethylene glycol bis-methacrylate, may be used as a cross-linking substance.

Another example of a material suitable for the member according to the invention is a copolymer of a hydrophilic monomer and a hydrophobic monomer. With this material, the capacity to absorb water and hence the swelling can be varied within wide limits by variation of the proportions between the hydrophilic and the hydrophobic monomers. Examples of the hydrophilic components are monomers in the group consisting of N-vinyl-pyrrolidones and vinyl pyridines and examples of the hydrophobic components are monomers in the group consisting of methylacrylate and methylmethacrylate. The polymerization may appropriately be effected in that the raw material is exposed to electromagnetic radiation in the ultraviolet-gamma radiation range or by heating. Suitable spermicides include nonoxinol-9 and other such chemical compositions, as is well known to those of ordinary skill in the art.

Figure 6:
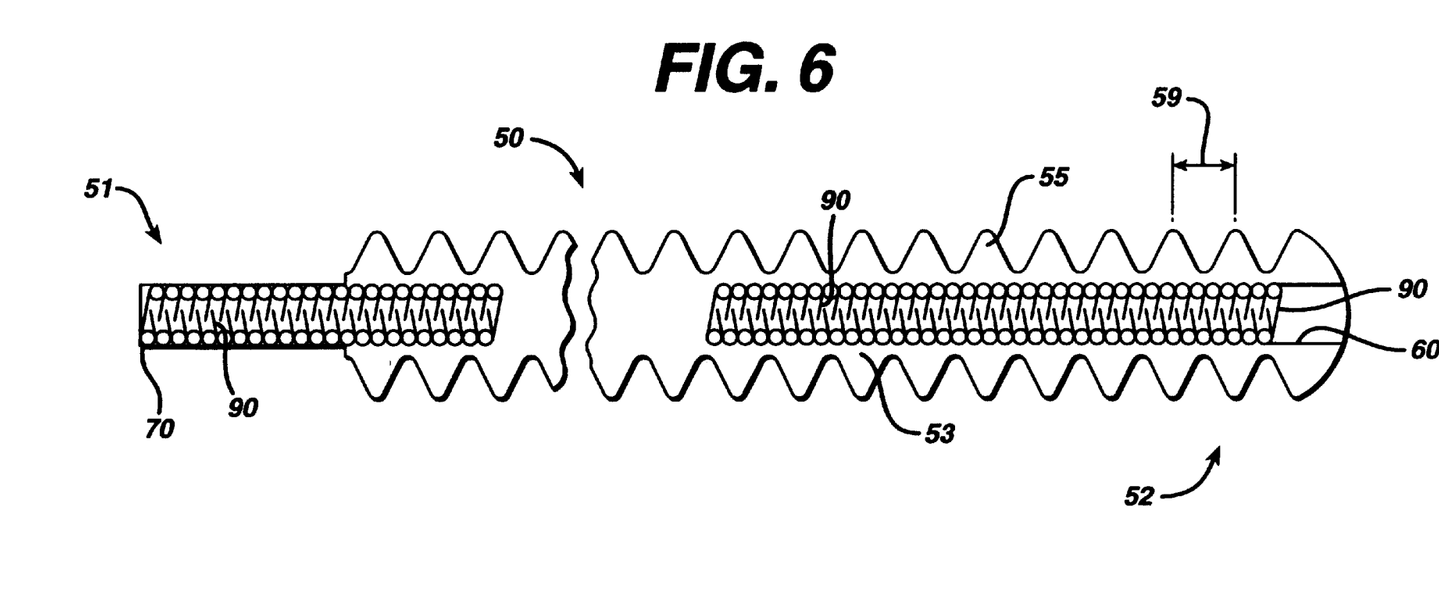
FIG. 6 is a side cross-sectional view of an embodiment of the present invention having a plurality of bristles disposed within the lumen of the blockage device body.

As shown in FIG. 6, the lumen 60 of the occlusive device 50 may be configured with a tortuous path of multiple bristles 90 lining the inner lumen of the occlusive device. Alternative methods of blocking the lumen are contemplated by the present invention, such as two helically wrapped flukes or blades within the lumen. Similarly, a spiral ribbon provides an essentially fluid-tight seal and a fatally long and tortuous path for migration of an ovum or spermatozoa.

Figures 7, 8:
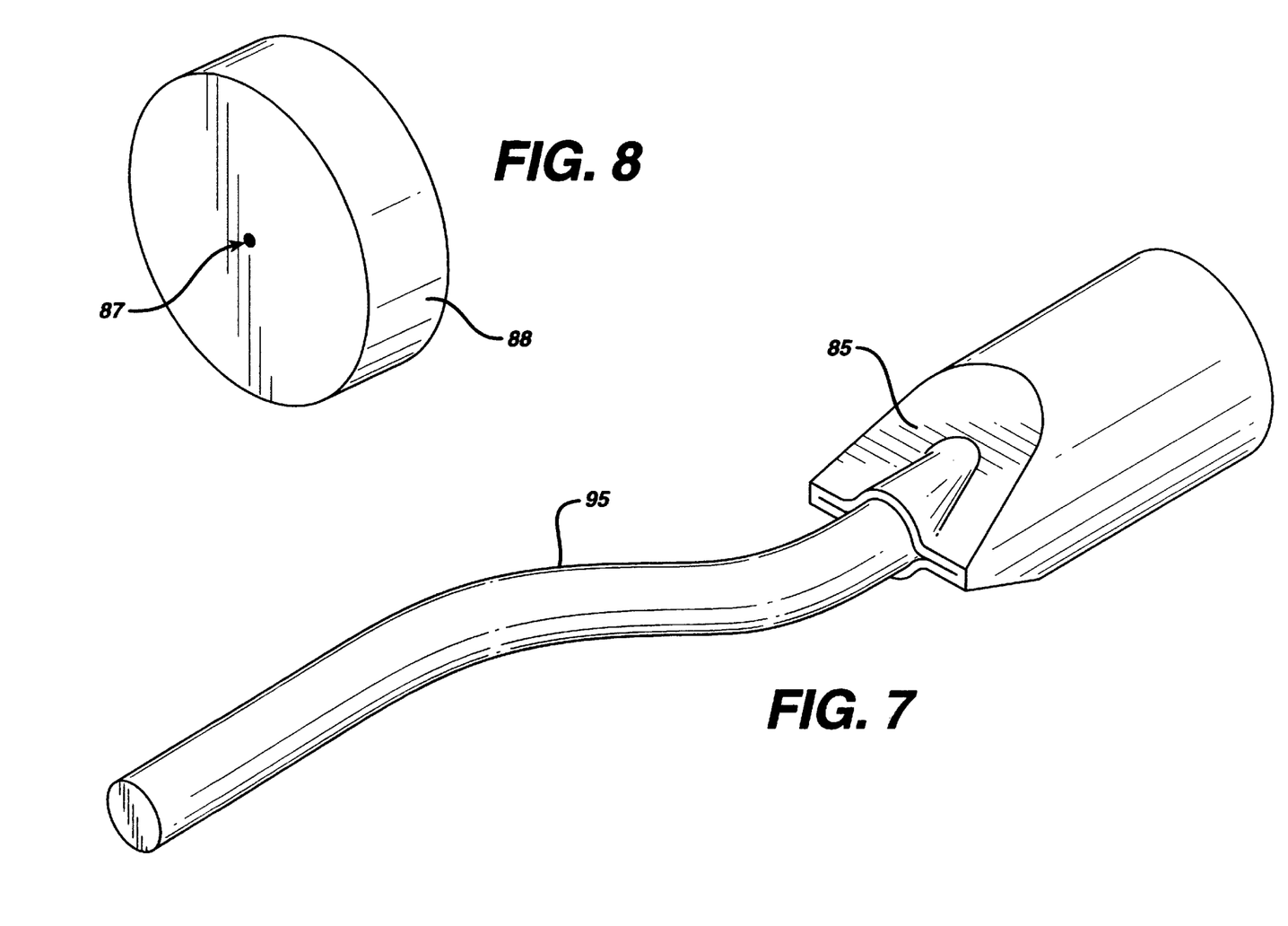
FIG. 7 is a perspective view of a guide wire retained in a duck bill valve formed in the distal end of an embodiment of the blockage device of the present invention.
FIG. 8 is a perspective view of a pinhole valve formed from an elastomeric material suitable for use in the blockage device of the present invention.

With reference to FIG. 7, a duckbill valve 85 may be secured to the distal end 52 and the proximal end 51 of the occlusive device 50. The duck bill valve provides a seal at each end of the lumen 60 of the blockage device. A first valve provides a seal around the guide wire 95 at the conical tip 65 to prevent ovum entry into the lumen of the occlusive device. Similarly, a second duckbill valve is disposed proximate the proximal end of the occlusive device to form a seal around the guide wire and to prevent sperm entry into the lumen of the occlusive device. Other valve types known to provide hermetic seals in medical devices may also be used within the lumen of the occlusive device. For example, and as shown in FIG. 8, a pinhole aperture 87 may be formed in an plug elastomeric material 88, such as silicone rubber or neoprene rubber, which is disposed in the distal and proximal ends of the blockage device lumen.

Figure 9A:
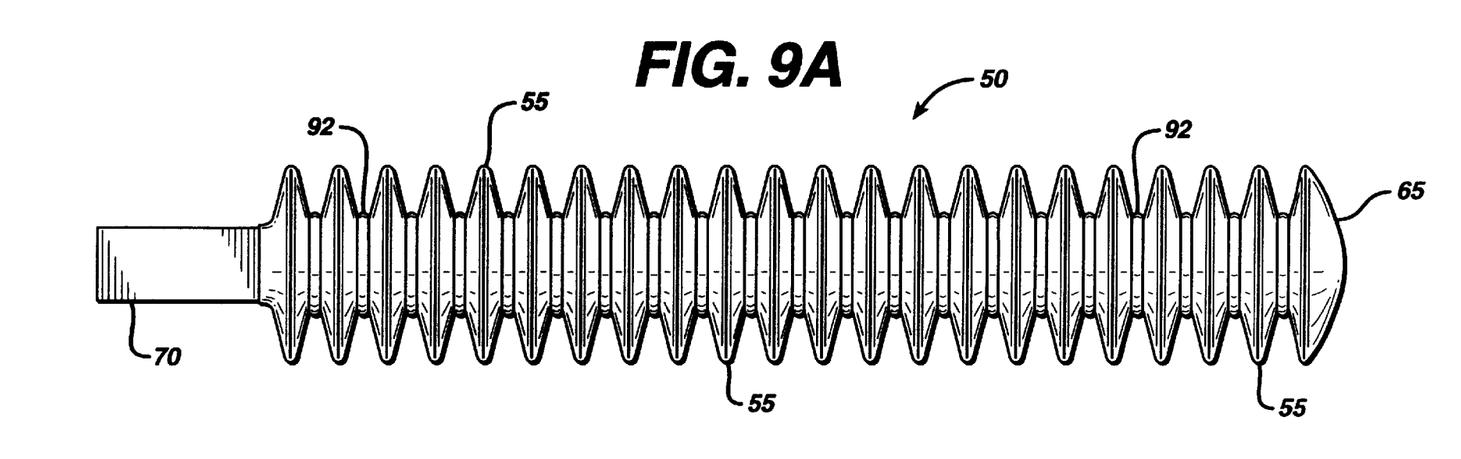
FIG. 9A is a side view of an embodiment of the present invention having a plurality of copper rings disposed between the ribs of the blockage device body.
Figure 9B:
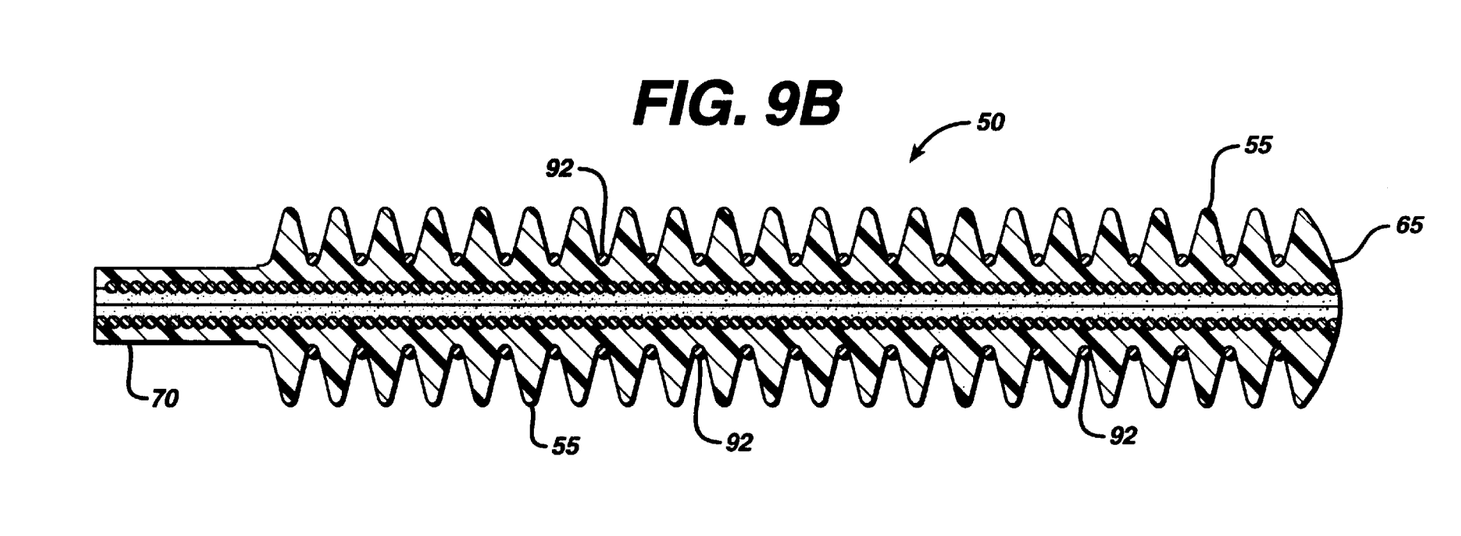
FIG. 9B is a side cross-sectional view of the blockage device shown in FIG. 9A.
Figure 10A:
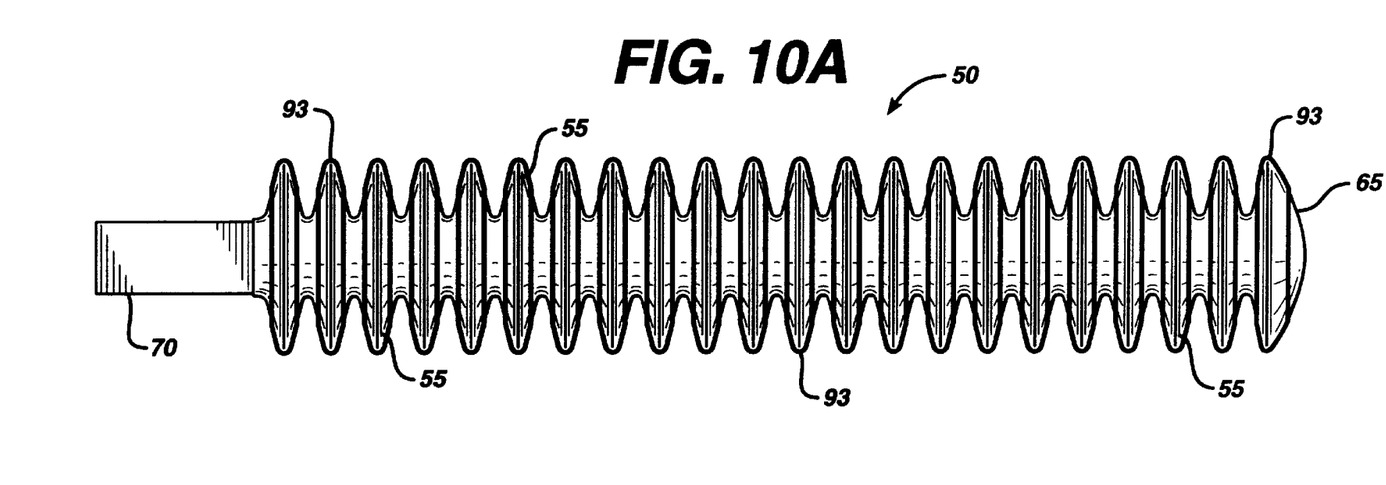
FIG. 10A is a side view of an embodiment of the present invention having a plurality of copper coated ribs formed in the blockage device body.
Figure 10B:
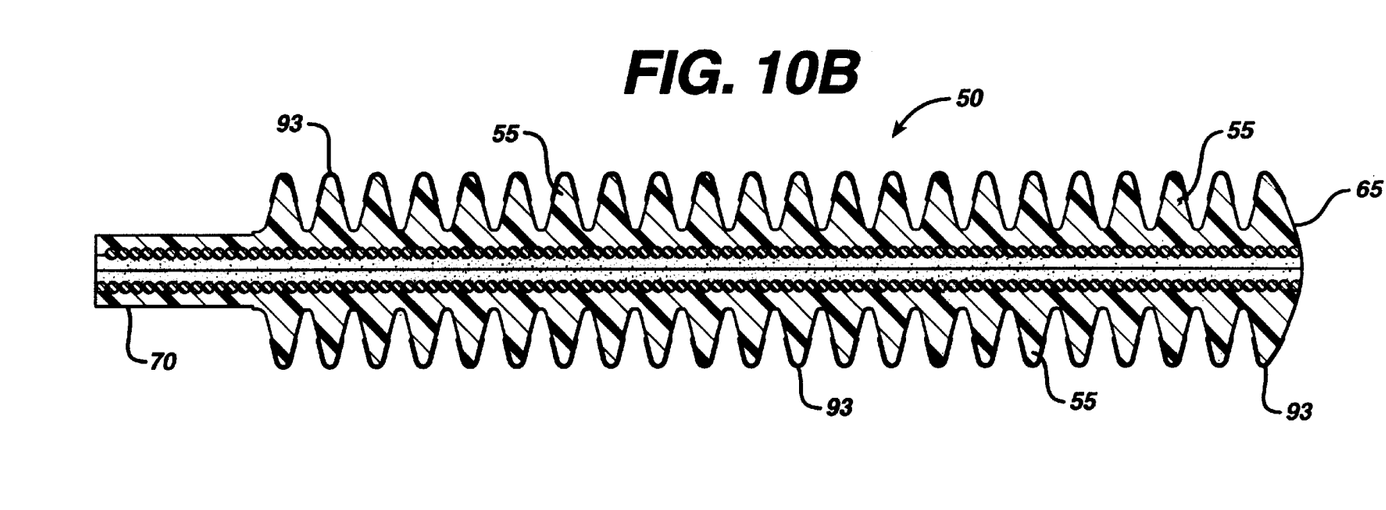
FIG. 10B is a side cross-sectional view of the blockage device as shown in FIG. 10A.

As shown in FIGS. 9A and 9B, a plurality of copper rings 92 may be disposed on the outer surface of the body 53 of the occlusive device 50. The copper rings are preferably disposed between the ribs or flukes 55 of the blockage device. It is well known in the art of contraception that copper kills, destroys or otherwise renders infertile a human female ovum. Thus, the addition of copper rings to the blockage device aids in preventing conception should the ovum traverse the occlusive device, pass through the Fallopian tube 30, 31 and migrate into the uterine cavity 28. Similarly, and as shown in FIGS. 10A and 10B, the outer surface of the occlusive device ribs may contain or be deposited with a copper coating 93. Such a copper coating serves to destroy the fertility of the ovum.

Figure 11:
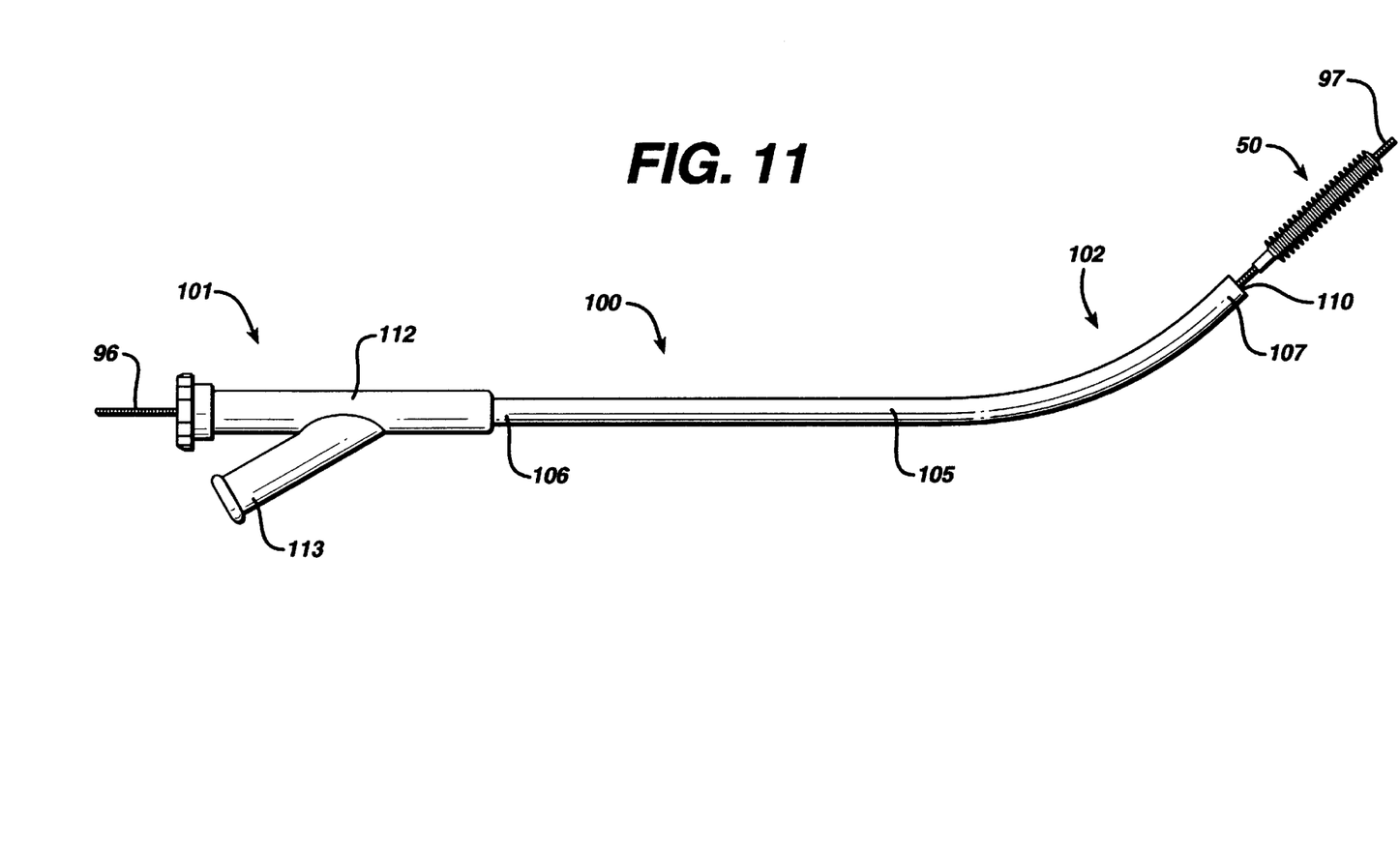
FIG. 11 is a side view of the blockage device, guide wire and delivery catheter of the present invention.

As shown in FIG. 11, the tubular occlusive device 50 of the present invention is disposed within a delivery catheter 100 or similar delivery device prior to deployment. The distal portion 102 of the catheter comprises a sheath 105 having a hollow lumen 110 for removably retaining the occlusive device. The distal portion of the catheter is formed with a curve so as to aid in directing the distal end 107 of the sheath toward the cornu 38 of the uterus 20. The proximal portion 101 of the catheter includes a wye adapter 112, for example, a Touhy-Borst adapter, secured to the proximal end 106 of the catheter sheath.

Prior to deployment, the occlusive device 50 is placed in the lumen 110 in the distal end 107 of the catheter sheath 105. A guide wire 95 is disposed within the delivery catheter 100 and through the lumen of the catheter sheath. The guide wire distal end 97 traverses the lumen 60 of the occlusive device. The proximal end 96 of the guide wire traverses through the wye adapter 112 which includes a silicone or otherwise fluid tight seal around the guide wire. A fluid injection port 113 allows injection of medicaments or contrast media through the catheter and into the uterus 20. In one embodiment, the body of the catheter is made very floppy to aid in the navigation and placement of the blocking device. If, however, the catheter is configured somewhat rigid, then the occlusive device can be "pushed" through the distal end of the catheter and into the desired location of the Fallopian tube 30, 31. Alternatively, the delivery catheter may be configured such that pressurizing the delivery catheter lumen will blow or otherwise force the occlusive device out the distal end of the delivery catheter.

Figure 12:
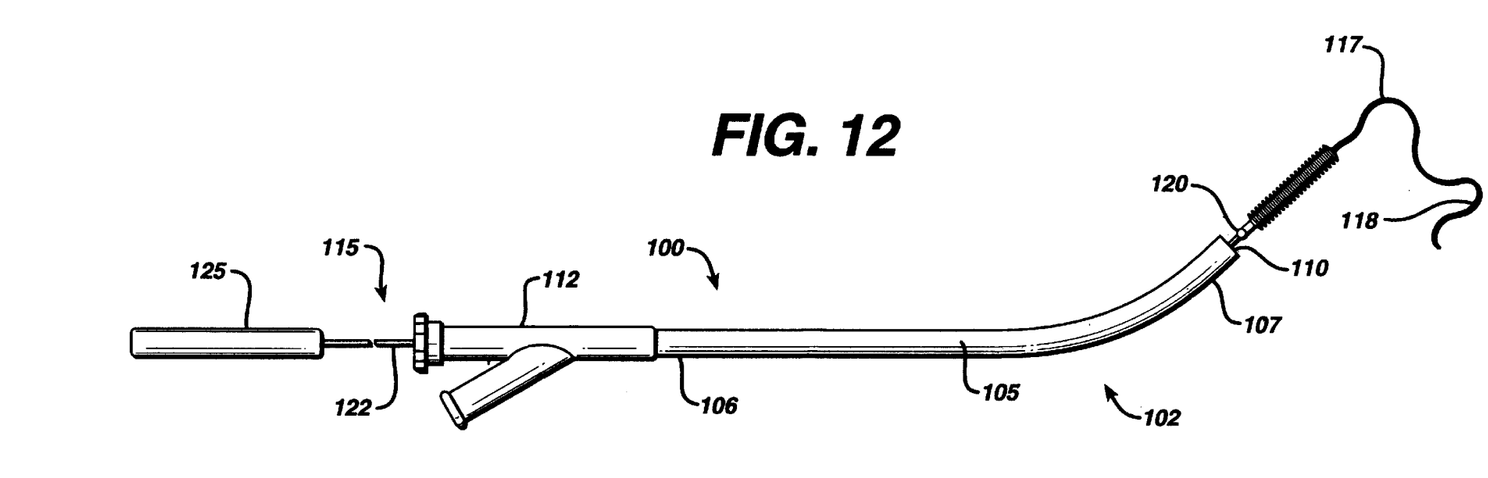
FIG. 12 is a side view of the blockage device, guide wire and delivery catheter including a handle assembly of the present invention.
Figure 13:
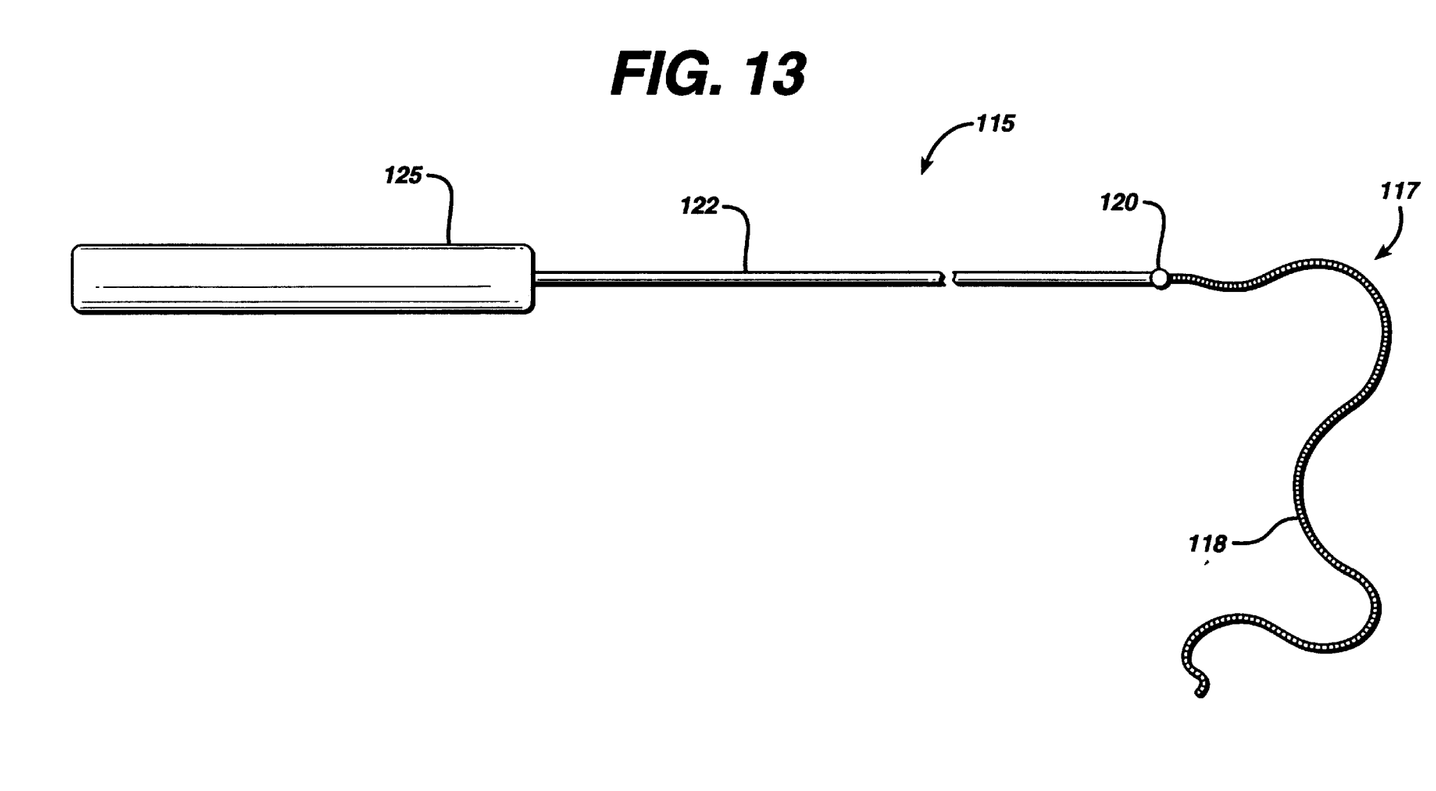
FIG. 13 is a side view of the handle assembly shown in FIG. 12.

As shown in FIGS. 12 and 13, an activator mechanism 115 is preferably provided with the sterilization system to enhance delivery of the occlusive device 50. A modified guide wire 117 includes a pusher button or obturator portion 120 which engages the flange 70 configured at the proximal end 51 of the occlusive device, adjacent the proximal rib 56. When the distal end 102 of the delivery catheter is positioned distal of the tubular ostium, the pusher button is placed into engagement with the occlusive device flange. Thus, when the distal end of the delivery catheter is properly placed, the guide wire or obturator may be used to deploy the occlusive device from the catheter and into the fallopian tube 30, 31. The distal end 107 of sheath portion 105 of the delivery catheter should be soft or semi-rigid and non-abrasive to the Fallopian tube wall 32.

As is also shown in FIGS. 12 and 13, a handle 125 may be secured to the proximal end of the activator mechanism 115 for manipulation of the guide wire 117 and ejection of the occlusive device 50. A rigid section 122, for example hypotube, extends distally from the handle and into the wye adapter 112 of the delivery catheter 100. A ball or pusher button 120 is disposed at the distal end of the rigid section for ejecting the occlusive device from the distal end 107 of the sheath 105. Prior to deployment, the occlusive device 50 is threaded over the floppy distal end 118 of the guide wire, which remains flexible and torqueable so as to be guided into the Fallopian tube 30, 31. Once the distal end of the catheter is disposed within the tubular os 42, the handle is pushed distally toward the wye adapter so that the pusher button engages the proximal end 70 of the occlusive device, thereby pushing the occlusive device through and out of the distal end of the deployment catheter and into the Fallopian tube interstitial section 34.

The sheath 105 of the delivery catheter 100 is formed from an elongated tubing made of semi-rigid material, for example, acrylonitrile-butadiene-styrene (ABS), polyvinylchloride (PVC) or polyurethane to permit easier insertion into the uterus. Such material provides the support needed to manipulate the catheter through the cervical canal 46 and into the uterine cavity 28. The catheter material must be flexible enough to follow the path of the guide wire 95, 117, while torqueable enough to be placed adjacent the interstitial portion 34 of a Fallopian tube 30, 31. The activator mechanism 115 may also be made of stainless steel ABS, PVC or similarly sturdy material. The guide wire is preferably made of stainless steel.

Figure 14:
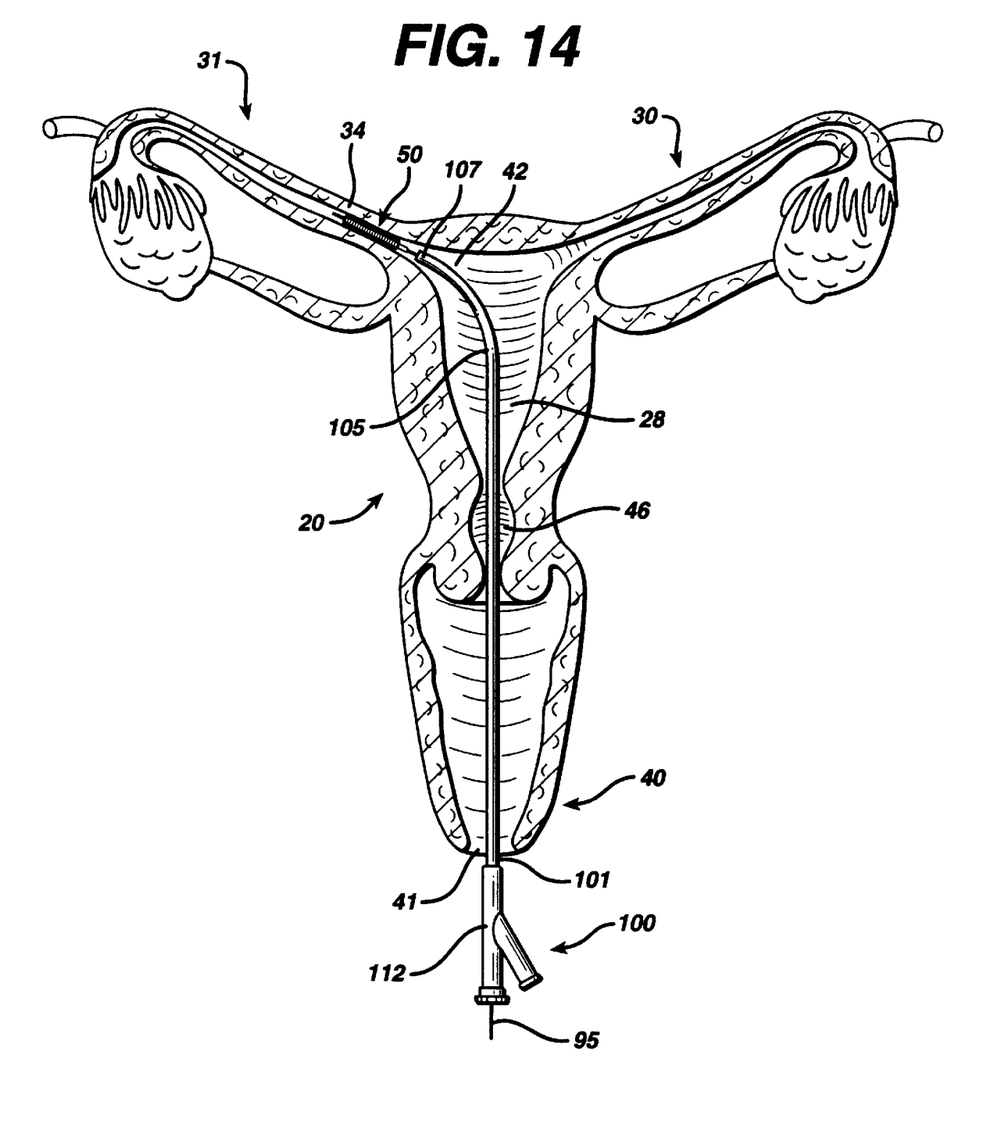
FIG. 14 is a front sectional view of the blockage device of the present invention released from the delivery catheter during deployment of the blockage device into the interstitial portion of a Fallopian tube.

As shown in FIG. 14, the method of the present invention includes loading the occlusive device 50 into the distal end 107 of the sheath 105 of the delivery catheter 100. A guide wire 95 is then threaded through the wye adapter 112 and the delivery catheter proximal end 101. The guide wire is further threaded through the catheter lumen 110 and into the proximal end 51 of the delivery device. The guide wire is then threaded through the lumen 60 of the delivery device, then through the distal end 52 of the delivery device and out through the distal end 102 of the catheter. The delivery catheter may then placed within the working channel of an hysteroscope or inserted directly into the uterus 20.

The uterus 20 is first distended using a distention medium such as saline or $CO_2$. The working channel of the hysteroscope may be used to instill the distention medium. The hysteroscope is inserted into the vagina 40, through the cervical canal 46 and into the uterine cavity 28 of the patient. The distal end of the hysteroscope is positioned adjacent and proximate the tubular ostia 42 and cornu 38. Alternatively, the delivery catheter may be replaced within the working channel of the hysteroscope prior to insertion of the hysteroscope into the patient.

In another embodiment, the distal portion 102 of the delivery catheter 100 is sufficiently rigid to traverse the vaginal opening 41 and cervix 45 the human uterus 20. Such a catheter is configured to transcervically place the distal end 107 of the sheath 105 adjacent a tubular os 42. A guide wire 95 may be used to facilitate guidance of the delivery catheter through the tubular ostia when sufficiently distended such that the distal end of the catheter enters the Fallopian tube 31 and traverses near the interstitial portion 34 of the Fallopian tube.

Once the distal end 102 of the delivery catheter 100 is positioned at a place where the occlusive device 50 is to be deployed, a deployment guide wire or obturator 117 is placed within the working channel of the hysteroscope or through the lumen 110 of the delivery catheter. The obturator or pusher button 120 is engaged with the flange 70 at the proximal end 51 of the occlusive device. Force is then exerted on the obturator to push the delivery device through the distal end of the delivery catheter and into the Fallopian tube 31. Alternatively, the catheter can be configured to slowly withdraw as the obturator or pusher guide wire holds the occlusive device in place within the Fallopian tube. The delivery catheter is then removed from the uterus 20, cervix 45 and vagina 40. The distention fluid may then be removed from the uterus. The procedure is then repeated for the contralateral Fallopian tube.

The method of sterilization of the present invention may be reversible. The occlusive device 50 may be removed by distending the uterus 20 and positioning a removal catheter proximate the occlusive device proximal end 51. Such removal catheters are generally well known in the art. The removal flange 70 configured at the proximal end of the occlusive device may be threaded so as to engage a screw-like removal device. Likewise, the occlusive device proximal end may be square, hexagon or octagon shaped to engage a grasping-type device (basket catheter). Alternatively, the occlusive device may be configured with a small loop for easy engagement. In addition, the occlusive device may be configured with hooks at its distal end 52, which engage the Fallopian tube wall 32 upon deployment and may be disengaged by pulling on a loop or similar mechanism configured in the occlusive device.

It will be apparent from the foregoing that, while particular forms of the invention have been illustrated and described, various modifications can be made without departing from the spirit and scope of the invention. Accordingly, it is not intended that the invention be limited, except as by the appended claims.

We claim:

1. An apparatus for human female sterilization, the apparatus comprising:

an elongate tubular member having a proximal end and a distal end, said tubular member having a lumen extending therethrough and in fluid communication with the proximal end and the distal end;

a flange formed at the proximal end of said elongate tubular member;

a plurality of ribs formed between the proximal end and the distal end of said tubular member; and a valve member disposed within the lumen of said tubular member.

2. The apparatus of claim 1, wherein the ribs of said tubular member are configured to be 1.5 to 10.0 times the diameter of a human fallopian tube.

3. The apparatus of claim 2, wherein the ribs of said tubular member are constructed of an elastomeric material.

4. The apparatus of claim 3, wherein the elastomeric material is latex rubber.

5. The apparatus of claim 4, wherein the valve member is configured from a hydrogel.

6. The apparatus of claim 5, wherein the hydrogel of said valve member is impregnated with a sterilization medium.

7. The apparatus of claim 1, wherein the valve member is configured with a plurality of bristles.

8. The apparatus of claim 1, wherein the valve member is configured with a duck-bill valve.

9. The apparatus of claim 1, wherein the valve member is configured with a plug having a pinhole aperture.

10. The apparatus of claim 1, further comprising a plurality of copper rings disposed between the ribs of said tubular member.

11. The apparatus of claim 1, further comprising a plurality of rings configured from material containing copper, said rings being disposed between the ribs of said tubular member.

12. The apparatus of claim 1, wherein the ribs of said tubular member are coated with copper.

13. The apparatus of claim 1, wherein the ribs of said tubular member are coated with a material containing copper.

14. A system for human female sterilization, the system comprising:

an elongate tubular member having a proximal end and a distal end, said tubular member having a lumen extending therethrough and in fluid communication with the proximal end and the distal end;

a flange formed proximate the proximal end of said elongate tubular member;

a plurality of ribs formed between the proximal end and the distal end of said tubular member;

a valve member disposed within the lumen of said tubular member; and a delivery catheter having a proximal end, a distal end and a lumen therethrough, wherein the distal end is configured for removably retaining said tubular member.

15. The system of claim 14, wherein said delivery catheter further comprises a wye adapter secured to the proximal end of said delivery catheter.

16. The system of claim 15, wherein said delivery catheter further comprises a handle secured to a guide wire, wherein the guide wire is partially disposed within the lumen of said delivery catheter and the handle is disposed proximal the wye adapter.

17. The system of claim 16, wherein said delivery catheter further comprises a pusher button secured proximate the proximal end of the guide wire and configured to engage the proximal end of said tubular member.

18. A method for human female sterilization, the method comprising:

(i) inserting into a Fallopian tube of human female uterus an elongate tubular member having a proximal end and a distal end, the tubular member including, (a) a lumen extending therethrough and in fluid communication with the proximal end and the distal end of the tubular member;

(b) a flange formed proximate the proximal end of the elongate tubular member;

(c) a plurality of ribs formed between the proximal end and the distal end of the tubular member; and (d) a valve member disposed within the lumen of said tubular member.

19. The method of claim 18, further comprising the steps of:

(ii) placing the tubular member within a delivery catheter having a lumen;

(iii) placing the delivery catheter within the uterus; and (iv) removing the tubular member from the delivery catheter and into the Fallopian tube.

20. The method of claim 19, wherein step (ii) further comprises the steps of:

inserting a guide wire into a Fallopian tube of the uterus; and threading the tubular member and the delivery catheter over the guide wire.

21. The method of claim 20 wherein step (iv) further comprises the step of:

removing the guide wire from the tubular member.

* * * * *